(12) United States Patent
O'Lenick et al.

(10) Patent No.: US 8,377,457 B1
(45) Date of Patent: Feb. 19, 2013

(54) NATURALLY DERIVED GLYCERYL DIMER POLYESTERS HAVING LIQUID AND SOLID DOMAINS

(75) Inventors: Kevin A. O'Lenick, Dacula, GA (US); Andrew J. O'Lenick, Dacula, GA (US); Anthony J. O'Lenick, Jr., Dacula, GA (US)

(73) Assignee: SurfaTech Corporation, Lawrenceville, GA (US)

( * ) Notice: Subject to any disclaimer, the term of this patent is extended or adjusted under 35 U.S.C. 154(b) by 395 days.

(21) Appl. No.: 12/660,123

(22) Filed: Feb. 22, 2010

Related U.S. Application Data

(60) Provisional application No. 61/274,562, filed on Aug. 20, 2009.

(51) Int. Cl.
*A61K 8/02* (2006.01)
*A61K 8/72* (2006.01)
*A61K 8/84* (2006.01)
*A61Q 5/12* (2006.01)
*C08G 63/54* (2006.01)

(52) U.S. Cl. ............... 424/401; 424/70.11; 424/400; 528/295.3

(58) Field of Classification Search .............. 528/295.3
See application file for complete search history.

(56) References Cited

U.S. PATENT DOCUMENTS

| 2,537,493 | A | * | 1/1951 | Thurston et al. | ............ 564/152 |
| 6,180,668 | B1 | | 1/2001 | O'Lenick | |
| 7,247,672 | B2 | * | 7/2007 | Tamazawa | ............ 524/588 |

OTHER PUBLICATIONS

Lin, KF; "Paints, Varnishes, and Related Products" Chapter 9 in Bailey's industrial Oil and Fat Products, Sixth Edition, 2005, edited by F. Shahidi, pp. 307-351.*

* cited by examiner

*Primary Examiner* — Ernst Arnold
*Assistant Examiner* — Christopher R Lea

(57) ABSTRACT

The present invention is directed to a series of polymeric glyceryl esters that have two different molecular weight ester chains, one solid and one liquid, which when combined into a single molecule make a polymer that is solid, and crosslinked by dimer acid. These products have very unique skin feel and water proofing properties. These materials find applications as additives to formulations in personal care products where there is a desire to have a structured film (provided by the solid fatty group) and flow properties, (provided by the liquid fatty group). These compounds by virtue of their unique structure provide outstanding skin feel.

12 Claims, No Drawings

NATURALLY DERIVED GLYCERYL DIMER POLYESTERS HAVING LIQUID AND SOLID DOMAINS

RELATED APPLICATIONS

This application claims priority to and benefit of U.S. Provisional Application No. 61/274,562 filed Aug. 20, 2009, the disclosure of which is incorporated herein for all purposes.

FIELD OF THE INVENTION

The present invention is directed to a series of polymeric glyceryl esters that have two different molecular weight ester chains, one solid and one liquid, which when combined into a single molecule make a polymer that is solid, but has very unique flow properties. These materials find applications as additives to formulations in personal care products where there is a desire to have a structured film (provided by the solid fatty group) and flow properties, (provided by the liquid fatty group). These compounds by virtue of their unique structure provide outstanding skin feel.

BACKGROUND OF THE INVENTION

Triglycerides are common natural materials. The structure is:

$$\begin{array}{l} CH_2-O-C(O)-R \\ CH-O-C(O)-R \\ CH_2-O-C(O)-R \end{array}$$

Triglycerides are esters that are the reaction product of glycerin (the alcohol portion) and fatty acids (the acid portion).

$$\begin{array}{l} \text{Ester bond} \\ \searrow \\ CH_2O\text{——}CO\text{——}R^{I} \\ CHO\text{——}CO\text{——}R^{II} \\ CH_2O\text{——}CO\text{——}R^{III} \end{array}$$
Alcohol    Acids Triglycerides include what are commonly called oils, fats, butters and waxes, terms that have been misused over the years. The historical definition of wax has previous been given. Butters, oils and fats are all triglycerides. Fats have a titer point of over 40.5° C., oils have a titer point of below 40.5° C. Butters have a titer below 40.5° C. but above 20° C. Oils are liquid at room temperature and we now use this word to describe any compound that is a liquid and is insoluble in water. As a result, Jojoba is referred to as an oil, despite the fact it is really a liquid wax.

Because oils, fats, butters and waxes are complex mixtures of homologues of similar chemical structures, it is difficult to obtain a true melting point. As the lower molecular weight fractions melt, they act as solvents to dissolve the higher molecular weight products. This results in a very wide melting "range" for these compounds. For this reason, titer point is generally determined on fats, oils, waxes and butters.

The titer is defined as the re-solidification point of the melted oil, fat butter or wax. The procedure is to heat the product to be tested until it is completely liquid, then to slowly cool with stirring. This is done until the temperature stays constant for 30 seconds, or begins to rise. The titer point is the highest temperature indicated by this rise.

Triglycerides are the tri-ester of glycerin with three equivalents of organic acid. Fatty acids are defined as those acids having alkyl or alkylene groups being C-5 and higher. The reaction is as follows:

$$\begin{array}{l} CH_2-OH \\ CH-OH \\ CH_2OH \end{array} + 3\ RC\overset{O}{\underset{\|}{-}}OH \longrightarrow \begin{array}{l} CH_2-OC(O)-R \\ CH-OC(O)-R \\ CH_2-O-C(O)-R \end{array} + 3\ H_2O$$

Glycerin    Fatty Acid          Triglyceride          Water

Triglycerides can be made in the laboratory, but occur commonly in nature. It is the commonly occurring natural triglycerides that are the materials of interest in the present invention.

U.S. Pat. No. 2,914,546 to Barsky et al teaches interesterification of mixed glyceryl compounds.

U.S. Pat. No. 6,306,906 to Wohlman and O'Lenick teach a process for conditioning hair and skin which comprise contacting the skin or hair with an effective conditioning concentration of a of the reaction product of meadowfoam oil and an ester selected from the group consisting of beeswax, jojoba oil, carnauba wax, and candelilla wax.

U.S. Pat. No. 6,180,668 to Wohlman and O'Lenick disclose a series of "reconstituted meadowfoam oils", used on skin for moisturizing and emollient applications. The term reconstituted as used hereon refers to a process in which meadowfoam oil and one or more oils of natural origin are transesterified under conditions of high temperature and catalyst to make a "reconstituted product" having an altered alkyl distribution and consequently altered chemical and physical properties.

These referenced patents are incorporated herein by reference.

None of these patents provide polyester derivatives of mixed fatty esters of glyceryl as envisioned by the present invention. Specifically, they lack the critical crosslinking diacid and the combination of liquid and solid domain groups critical to the properties of the present invention.

THE INVENTION

Objective of the Invention

The present invention has as its objective a series of glyceryl polyesters that have both liquid and solid fatty groups contained thereon and are crosslinked by diacids and contain fatty groups, one solid at room temperature, the other liquid at room temperature.

The present invention also has an objective a process for treating hair and skin with the glyceryl multi domain polyesters that have both liquid and solid fatty groups contained thereon and are crosslinked by the diacid.

Other objectives will become clear as one reads the specification and claims herein.

SUMMARY OF THE INVENTION

The present invention discloses a polyester made by the reaction of a mixture of liquid and solid fatty acids reacted with citric acid and a diacid crosslinker.

DETAILED DESCRIPTION OF THE INVENTION

The products of the present invention are made by the esterification reaction of:

(a) glycerin conforming to the following structure:

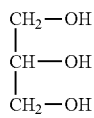

(b) dimer acid which conforms to the following structure:

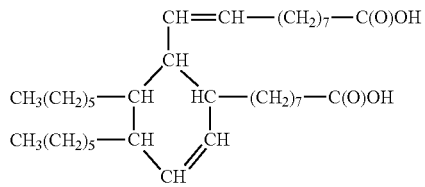

(c) oleic acid conforming to the following structure:

resulting in liquid high molecular weight domains (d) a fatty acid that is solid at room temperature

b is an integer ranging from 10 to 30 (resulting in solid domains).

Another aspect of the present invention is a process for conditioning hair and skin which comprises contacting the hair or skin with an effective conditioning concentration of a polyester made by the esterification reaction of:

(a) glycerin conforming to the following structure:

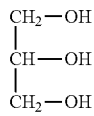

(b) oleic acid conforming to the following structure:

resulting in liquid high molecular weight domains
and (c) a fatty acid that is solid at room temperature

b is an integer ranging from 10 to 30 (resulting in solid domains).

followed by reaction with a diacid conforming to the following structure:

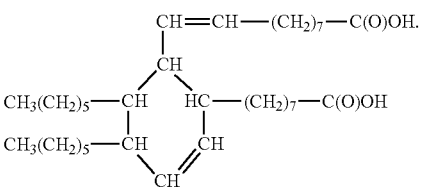

Where there are two different types of ester group present, one liquid and one solid, the resulting structure cannot crystallize completely, since the liquid domains in the polymer act as molecular crystal distorters, resulting in a polymer that although having the same melting point, flows more easily when pressure is applied. The resulting solid will be soft and flowable, rather than hard and un-yielding.

Preferred Embodiments

In a preferred embodiment b is 18.
In a preferred embodiment b is 16
In a preferred embodiment b is an integer ranging from 16 to 20.
In a preferred embodiment b is 16.

EXAMPLES

Example 1

Glycerin

Glycerin is an item of commerce commercially available from a variety of sources including Proctor and Gamble. It conforms to the following structure:

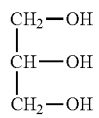

CAS Registry Number: 56-81-5

Example 2

Dimer Acid

Dimer acid is an item of commerce available from a variety of sources including Cognis. It conforms to the following structure:

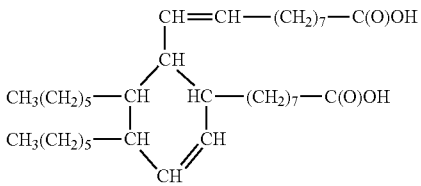

In the present invention this material provides a linking group that is (a) natural, (b) free of polyoxyethylene and polyoxypropylene compounds and their inherent ether groups and lack of natural origin, and (c) are easily reacted into the polymer matrix.

The inclusion of this high molecular weight acid results in considerable barrier properties when the polymers of the present invention are applied to the skin.

Example 3

Oleic Acid

Oleic acid commercially available from a variety of sources including Cognis.

$CH_3—(CH_2)_7—CH=CH—(CH_2)_7—C(O)—OH$

Examples 4-9

Fatty Acids (Solid at Room Temperature)

These acids are an item of commerce available from a variety of sources. It conforms to the following structure;

$HO—C(O)(CH_2)_b—CH_3$ b is an integer ranging from 10 to 30.

| Example | b |
|---------|----|
| 4 | 10 |
| 5 | 12 |
| 6 | 14 |
| 7 | 16 |
| 8 | 18 |
| 9 | 30 |

To a suitable reactor equipped with heating and an ability to distill off water is added the specified number of grams of glycerin (Example 1), next is added the specified number of grams of the oleic acid (Example 3). Finally, is added the specified number of grams of the specified solid fatty alcohol (Examples 4-9). The reaction mass is heated to 150-160° C. and water is distilled off. As the reaction proceeds, the batch clears and free citric acid is reacted out. The reaction mass is kept at this temperature until the acid value becomes vanishingly low. Next is added the specified number of grams of the specified diacid (Examples 2-4). The reaction mass is heated to 180-190° C. and water is distilled off. The reaction mass is kept at this temperature until the acid value becomes vanishingly low. The reaction mass is cooled and used without additional purification.

| Ex-ample | Glycerin | | Dimer acid | | Oleic Acid | | Solid Acid | | a value |
|---|---|---|---|---|---|---|---|---|---|
| | Ex | Grams | Ex | Grams | Ex | Grams | Ex. | Grams | |
| 12 | 1 | 270 | 2 | 1200 | 3 | 1705 | 4 | 460 | 1 |
| 13 | 1 | 360 | 3 | 1800 | 3 | 1410 | 5 | 212 | 2 |
| 14 | 1 | 630 | 4 | 3600 | 3 | 1410 | 6 | 960 | 5 |
| 15 | 1 | 1080 | 2 | 6600 | 3 | 1974 | 7 | 1876 | 10 |
| 16 | 1 | 1980 | 3 | 12600 | 3 | 5640 | 8 | 1184 | 20 |
| 17 | 1 | 270 | 4 | 1200 | 3 | 564 | 9 | 1392 | 1 |
| 18 | 1 | 1980 | 3 | 12600 | 3 | 1128 | 4 | 3680 | 20 |
| 19 | 1 | 1080 | 4 | 6600 | 3 | 1692 | 5 | 1696 | 10 |
| 20 | 1 | 630 | 2 | 2400 | 3 | 564 | 6 | 1680 | 3 |
| 21 | 1 | 450 | 4 | 3600 | 3 | 1128 | 7 | 804 | 5 |
| 22 | 1 | 180 | 2 | 600 | 3 | 564 | 8 | 592 | 0 |
| 23 | 1 | 630 | 3 | 630 | 3 | 564 | 9 | 3284 | 5 |

Ex means example in the table above.

Products that are of the present invention were low order soft pastes that liquefied under pressure.

The compounds are of exceptional interest in the personal care applications where gloss, rheology that accommodates spreading and odor are critical.

They provide waterproofing properties when applied to skin.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. A polyester made by the esterification reaction consisting essentially of:
   (a) glycerin;
   (b) a dimer acid of the structure:

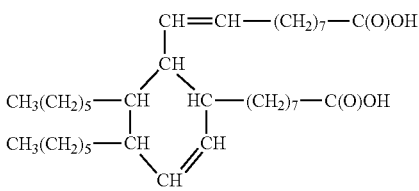

(c) oleic acid; and
   (d) a solid fatty acid having the formula:

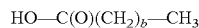
$HO—C(O)(CH_2)_b—CH_3$ b is an integer ranging from 10 to 30;
   with the proviso that the ratio of oleic to solid acid ranges from 0.2 to 6.7.

2. A polyester of claim 1 wherein b is 18.
3. A polyester of claim 1 wherein b is 16.
4. A polyester of claim 1 wherein b is an integer ranging from 16 to 20.
5. A process for conditioning hair and skin which comprises contacting the hair or skin with an effective conditioning concentration of a polyester of claim 1.
6. A process of claim 5 wherein b is 18.
7. A process of claim 5 wherein b is 16.
8. A process of claim 5 wherein b is an integer ranging from 16 to 20.
9. A process of claim 5 wherein said effective conditioning concentration ranges from 0.1% to 20% by weight.
10. A process of claim 9 wherein b is 18.
11. A process of claim 9 wherein b is 16.
12. A process of claim 9 wherein b is an integer ranging from 16 to 20.

* * * * *